(12) United States Patent
Middleton et al.

(10) Patent No.: US 11,291,680 B2
(45) Date of Patent: Apr. 5, 2022

(54) COMPOSITIONS AND METHODS THAT MODULATE WHITE BLOOD CELLS OR NEUTROPHILS IN A COMPANION ANIMAL

(71) Applicant: NESTEC SA, Vevey (CH)

(72) Inventors: Rondo P Middleton, Creve Coeur, MO (US); Brian M Zanghi, Ballwin, MO (US); Serge Andre Dominique Rezzi, Semsales (CH); Steven S Hannah, Chesterfield, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 331 days.

(21) Appl. No.: 15/839,359

(22) Filed: Dec. 12, 2017

(65) Prior Publication Data

US 2018/0169127 A1   Jun. 21, 2018

Related U.S. Application Data

(60) Provisional application No. 62/434,534, filed on Dec. 15, 2016.

(51) Int. Cl.

| | |
|---|---|
| *A23K 20/147* | (2016.01) |
| *A23K 20/158* | (2016.01) |
| *A61K 31/198* | (2006.01) |
| *A61K 31/405* | (2006.01) |
| *A61K 31/7056* | (2006.01) |
| *A23K 10/00* | (2016.01) |
| *A23K 20/00* | (2016.01) |
| *A23K 20/10* | (2016.01) |
| *A23K 20/163* | (2016.01) |
| *A23K 50/42* | (2016.01) |
| *A23K 50/48* | (2016.01) |
| *A61K 31/194* | (2006.01) |
| *A61K 31/197* | (2006.01) |
| *A61K 31/225* | (2006.01) |
| *A61K 31/23* | (2006.01) |
| *A61K 31/235* | (2006.01) |
| *A61K 31/255* | (2006.01) |
| *A61K 31/683* | (2006.01) |
| *A61K 31/7072* | (2006.01) |
| *G01N 33/50* | (2006.01) |

(52) U.S. Cl.
CPC .......... *A61K 31/7056* (2013.01); *A23K 10/00* (2016.05); *A23K 20/00* (2016.05); *A23K 20/10* (2016.05); *A23K 20/147* (2016.05); *A23K 20/158* (2016.05); *A23K 20/163* (2016.05); *A23K 50/42* (2016.05); *A23K 50/48* (2016.05); *A61K 31/194* (2013.01); *A61K 31/197* (2013.01); *A61K 31/198* (2013.01); *A61K 31/225* (2013.01); *A61K 31/23* (2013.01); *A61K 31/235* (2013.01); *A61K 31/255* (2013.01); *A61K 31/405* (2013.01); *A61K 31/683* (2013.01); *A61K 31/7072* (2013.01); *G01N 33/5094* (2013.01)

(58) Field of Classification Search
None
See application file for complete search history.

(56) References Cited

U.S. PATENT DOCUMENTS

| | | |
|---|---|---|
| 5,693,533 A | 12/1997 | Raney et al. |
| 6,444,872 B1 | 9/2002 | Andersson et al. |
| 6,489,311 B1 | 12/2002 | Kennedy |
| 6,756,211 B1 | 6/2004 | Moyle et al. |
| 6,962,795 B1 | 11/2005 | Moyle et al. |
| 8,311,746 B2 | 11/2012 | Bauer et al. |
| 2002/0182276 A1* | 12/2002 | Wadsworth ............ A23K 10/30 424/765 |
| 2003/0162956 A1 | 8/2003 | Ni et al. |
| 2003/0224345 A1 | 12/2003 | West et al. |
| 2006/0063924 A1 | 3/2006 | Ni et al. |
| 2007/0026485 A1 | 2/2007 | DeFrees et al. |
| 2007/0078136 A1 | 4/2007 | Vaccaro et al. |
| 2010/0196880 A1 | 8/2010 | Satyaraj et al. |
| 2011/0059103 A1 | 3/2011 | Biessen et al. |
| 2011/0144312 A1 | 6/2011 | Kato et al. |
| 2011/0268763 A1 | 11/2011 | Marshall |
| 2014/0086881 A1 | 3/2014 | Hoang |
| 2015/0010669 A1 | 1/2015 | Kimura |
| 2015/0173333 A1 | 6/2015 | Ung et al. |
| 2015/0259742 A1 | 9/2015 | Zhang et al. |

(Continued)

FOREIGN PATENT DOCUMENTS

| | | |
|---|---|---|
| EP | 0061141 B1 | 7/1986 |
| EP | 0357672 B1 | 12/1995 |
| EP | 0731709 B1 | 10/2001 |

(Continued)

OTHER PUBLICATIONS

Lindsay, "Morinda citrifolia: Amino Acid and Lipid Content of the Noni Fruit at Various Stages of Maturity", Journal of Scientific Research, 4(2), 467-476, 2012 (Year: 2012).*

Hall, et al., "Dietary (N-3) fatty acids alter plasma fatty acids et al." Prostaglandins, Leukotrienes and Essential Fatty Acids 43(2005) 335-341.

(Continued)

*Primary Examiner* — Robert T. Crow
*Assistant Examiner* — John P Nguyen

(57) ABSTRACT

White blood cells and/or neutrophils in a companion animal can be improved by adjusting the diet of the animal to increase the amount of a compound which positively or negatively modulates the white blood cells and/or neutrophils or adjusting the diet of the animal to decrease the amount of a compound which positively or negatively modulates the white blood cells and/or neutrophils.

11 Claims, No Drawings

(56) References Cited

U.S. PATENT DOCUMENTS

2015/0284438 A1 10/2015 Sekaran et al.
2018/0168194 A1* 6/2018 Middleton ........... A23K 20/142

FOREIGN PATENT DOCUMENTS

| | | |
|---|---|---|
| EP | 0988861 B1 | 3/2004 |
| EP | 1699800 | 10/2010 |
| EP | 1684075 B1 | 11/2010 |
| EP | 2251333 A1 | 11/2010 |
| EP | 1641764 B1 | 7/2011 |
| EP | 1411967 B1 | 10/2011 |
| EP | 2551352 A1 | 1/2013 |
| EP | 1973573 B1 | 5/2013 |
| EP | 1472187 B1 | 6/2013 |
| EP | 1617876 B1 | 5/2014 |
| WO | 9844808 | 10/1998 |
| WO | 0065093 A2 | 11/2000 |
| WO | 2009052390 | 4/2009 |

OTHER PUBLICATIONS

Kraemer R, Bednar MM, Hatala MA, Mullane KM. A neutrophil-derived cytochrome P450-dependent metabolite of arachidonic acid modulates neutrophil behavior. Am J Pathol. Sep. 1987;128(3):446-54. PubMed PMID: 2820233; PubMed Central PMCID: PMC1899671.

Iverson S, Zahid N, Uetrecht JP. Predicting drug-induced agranulocytosis: characterizing neutrophil-generated metabolites of a model compound, DMP 406, and assessing the relevance of an in vitro apoptosis assay for identifying drugs that may cause agranulocytosis. Chem Biol Interact. Nov. 10, 2002;142(1-2): 175-99. JubMed PMID: 12399162.

International Search Report and Written Opinion, PCT/IB2017/057851, dated Mar. 23, 2018.

\* cited by examiner

COMPOSITIONS AND METHODS THAT MODULATE WHITE BLOOD CELLS OR NEUTROPHILS IN A COMPANION ANIMAL

CROSS REFERENCE TO RELATED APPLICATIONS

This application claims priority to U.S. Provisional Application Ser. No. 62/434,534 filed Dec. 15, 2016, the disclosure of which is incorporated in its entirety herein by this reference.

BACKGROUND

White blood cells (WBC), also referred to as leukocytes, are cells which help fight infections. WBCs consist of basophils, eosinophils, lymphocytes (T and B cells), monocytes and neutrophils. Low levels are indicative of bone marrow deficiencies, cancer treating drugs, diseases of the liver or spleen, some types of viral and bacterial infections, etc. High levels are indicative of some bacterial infections, physical stress, anemia, certain drugs, etc. Neutrophils are a type of white blood cell involved in protection against infection. When neutrophil levels are low, an organism is vulnerable to illness and infection. Low levels are indicative of many things including: vitamin B12 deficiency, bacterial infection, anemia, leukemia, medication effects, etc. High levels are indicative of: stress, bacterial infection, kidney failure, cancer, ketoacidosis and some medications. As such, both white blood cells and neutrophils are important to animal health.

SUMMARY

The present disclosure relates generally to pet food compositions; methods of minimizing costs associated with production of a pet food; methods of enhancing nutritional benefit of a pet food; and methods for modulating at least one of white blood cells or neutrophils in a companion animal. Specifically, the present disclosure relates to metabolites for modulating at least one of white blood cells or neutrophils in a companion animal.

The present inventors have developed a predictive model of white blood cells and neutrophils by identifying metabolite compounds which correlate to white blood cells or neutrophils. A very controlled study was employed to minimize other external factors by using multiple canines all fed the same diet. A validation model was then developed by feeding different levels of the identified compounds (via a dietary change) to a group of canines and measuring changes in the corresponding health parameter (i.e. white blood cells or neutrophils.

Accordingly, in a general embodiment, the present disclosure provides a pet food composition comprising: protein, carbohydrates, fat, fiber, and a metabolite for modulating at least one of white blood cells or neutrophils in a companion animal. In one embodiment, the pet food composition can provide at least a 5% increase or at least a 5% decrease in the amount of at least one of white blood cells or neutrophils in the companion animal. In one aspect, the pet food can provide an increase in white blood cells or neutrophils. In another aspect, the pet food can comprise a decrease in white blood cells or neutrophils.

The present disclosure also provides methods of minimizing costs associated with production of a pet food; methods of enhancing nutritional benefit of a pet food; methods for modulating at least one of white blood cells or neutrophils in a companion animal; and methods of measuring a change in the amount of at least one of white blood cells or neutrophils in a companion animal.

An advantage of one or more embodiments provided by the present disclosure is to improve white blood cells or neutrophils in a companion animal by adjusting the diet of the animal to increase the amount of a compound which positively modulates the white blood cells or neutrophils or to decrease the amount of a compound which negatively modulates the white blood cells or neutrophils.

Another advantage of one or more embodiments provided by the present disclosure is to minimize pet food production costs by utilizing ingredients which are appropriately high or low in the identified compounds or precursors thereof, as generally illustrated by the non-limiting examples discussed herein.

Additional features and advantages are described herein and will be apparent from the following Detailed Description.

DETAILED DESCRIPTION

Definitions

As used in this disclosure and the appended claims, the singular forms "a," "an" and "the" include plural referents unless the context clearly dictates otherwise. Thus, for example, reference to "a composition" or "the composition" includes two or more compositions. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the food composition unless expressed otherwise. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The terms "food," "food product" and "food composition" mean a product or composition that is intended for ingestion by an animal, including a human, and provides at least one nutrient to the animal. Further in this regard, these terms mean that the product or composition is in a form ready for consumption and is not merely an intermediate from which a consumable product or composition is made, although other food compositions can be added in some embodiments. The term "pet food" means any food composition intended to be consumed by a pet. The term "pet" means any animal which could benefit from or enjoy the compositions provided by the present disclosure. For example, the pet can be an avian, bovine, canine, equine, feline, hircine, lupine, murine, ovine, or porcine animal, but the pet can be any suitable animal.

The term "companion animal" means a dog or a cat. In an embodiment, the compositions and methods disclosed herein involve a senior dog or a senior cat. Dogs are considered senior in the last 25% of their lives. The life span of a dog depends on its size and/or its breed, but for the present disclosure a senior dog is a dog that is at least 5 years of age (e.g., at least 6 years of age, at least 7 years of age, or at least 8 years of age). The life span of a cat also depends on its size and/or its breed, but for the present disclosure a senior cat is a cat that is at least 7 years of age (e.g., at least 8 years of age, at least 9 years of age, or at least 10 years of age).

As used herein, "comparable companion animal" refers to a healthy animal of the same gender, breed, and age as the companion animal.

As used herein, "metabolite" refers to a compound having biological activity in a companion animal that is an intermediate or product of metabolism, and includes precursors thereof. As used herein, "precursor" refers to any compound that metabolizes to a metabolite during metabolism in a companion animal. For example, if the specific metabolite is cysteine, "the metabolite" comprises a cysteine precursor (e.g., methionine).

As used herein, "white blood cells" or "leukocytes" or "leucocytes" refer to the cells of the immune system that are involved in protecting the body against both infectious disease and foreign invaders. All white blood cells are produced and derived from multipotent cells in the bone marrow known as hematopoietic stem cells. Leukocytes are found throughout the body, including the blood and lymphatic system. In the various embodiments described herein, reference to white blood cells can exclude neutrophils when the use of the terms "white blood cells" and "neutrophils" are required to be exclusive.

As used herein, "neutrophils" or "neutrocytes" refer to the most abundant type of granulocytes and the most abundant (40% to 75%) type of white blood cells in most mammals and are a type of phagocyte and are normally found in the bloodstream.

The term "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In one embodiment, the present metabolite or combination of metabolites can be present in an effective amount for modulating white blood cells or neutrophils in a companion animal.

The dosages expressed herein are in milligrams per kilogram of body weight per day (mg/kg/day) unless expressed otherwise.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging animals, the animal will continue consuming on a regular basis for the remainder of its life. This can also be referred to as consumption for "extended" periods.

The term "regular basis" or "regular administration" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. The skilled artisan will appreciate that the blood level of a compound or certain metabolites of that compound or which result after the consumption of that compound, may be a useful tool for assessing or determining dosing frequency. For example, for determining feeding amounts for pet food compositions comprising a certain metabolite, the blood concentration of that metabolite, may provide useful information. A frequency, regardless of whether expressly exemplified herein, that allows maintenance of a desired blood level of the measured compound, such as a metabolite, within acceptable ranges can be useful herein. The skilled artisan will appreciate that feeding amounts will be a function of the composition that is being consumed or administered as well as the animal consuming the food, and some food compositions may require more or less frequent administration to maintain a desired blood level of the measured compound (e.g., a metabolite).

The relative terms "improve," "increase," "enhance," "decrease" and the like refer to the effects of the composition disclosed herein (a composition comprising a metabolites) relative to a composition having a lower amount or lacking such metabolites, but otherwise identical.

A "blended" composition merely has at least two components having at least one different characteristic relative to each other. In one aspect, moisture content and water activity can be different in the context of the present disclosure. In this regard, description of a composition as "blended" does not imply that the blended composition has been subjected to processing sometimes referenced as "blending," namely mixing components so that they are indistinguishable from each other, and, in one aspect, such processing is avoided when mixing one component with the other components to form a blended composition (e.g., mixing a dry component with a wet or semi-moist component). Further in this regard, in a blended composition each of the at least two components having at least one different characteristic relative to each other can retain their distinct identity and appearance.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "dietary supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

The present discussion of embodiments, aspects, examples, etc. are independent in that they can apply to all methods and compositions. For example, a metabolite used in a pet food composition can also be used in the method of modulating or a method of minimizing costs associated with making such a pet food, and vice versa.

Embodiments

In an aspect of the present disclosure, a pet food composition can comprise protein, carbohydrates, fat, fiber, and a metabolite for modulating at least one of white blood cells or neutrophils in a companion animal. In one aspect, the pet food composition can include at least 4 distinct metabolites including at least 2 distinct metabolites for modulating each one of white blood cells and neutrophils in a companion animal. In one embodiment, the pet food composition can provide an increase in at least one of white blood cells or neutrophils in the companion animal. In one aspect, the companion animal can be a senior dog or a senior cat.

In another aspect of the present disclosure, a method of modulating at least one of white blood cells or neutrophils in a companion animal is provided. The method comprises administering to the companion animal a pet food composition comprising protein, carbohydrates, fat, fiber, and a metabolite for modulating at least one of white blood cells or neutrophils in the companion animal. In one aspect, the companion animal can be a senior dog or a senior cat.

In still another aspect, a method of measuring a change in the amount of at least one of white blood cells or neutrophils in a companion animal can comprise obtaining a serum sample of the companion animal, measuring concentrations of at least three distinct metabolites from the serum sample that modulate at least one of white blood cells or neutrophils, and determining that the white blood cells or neutrophils has changed if, after comparing the metabolite concentrations to average metabolite concentrations of each metabolite from comparable companion animals, the metabolite concentrations are different than the average metabolite concentrations.

Yet another aspect of the present disclosure is a method of minimizing costs associated with production of a pet food having a first formulation designed for consumption by a companion animal, such as a senior dog or a senior cat. A further aspect of the present disclosure is a method of enhancing nutritional benefit of a pet food having a first formulation designed for consumption by a companion animal, such as a senior dog or a senior cat. These methods comprise adjusting the first formulation of the pet food to be a second formulation. At least one of the first and second formulations comprises a metabolite for modulating at least one of white blood cells or neutrophils in the companion animal. The adjusting comprises changing an amount of the metabolite in the first formulation to a different amount in the second formulation.

"Minimizing" costs means that the costs associated with making the second formulation are less than the costs associated with making the first formulation, for example on a per serving basis, per unit weight, per unit volume, per total energy, and the like. "Enhanced" nutritional benefit means that the nutritional benefit of the second formulation is greater than the nutritional benefit of the first formulation.

As discussed herein, the pet food compositions and methods can contain a metabolite or multiple metabolites for modulating white blood cells or neutrophils. In various aspects, the compositions and methods can contain 1, 2, 3, 4, 5, 6, 7, 8, 9, or even 10 metabolites for any one of white blood cells or neutrophils, or for both white blood cells and neutrophils. As such, in one embodiment, the composition can comprise at least 4 distinct metabolites, including at least 2 distinct metabolites for individually modulating each one of white blood cells and neutrophils in a companion animal. In another embodiment, the composition can comprise at least 6 distinct metabolites, including at least 3 distinct metabolites for individually modulating each one of white blood cells and neutrophils in a companion animal. In still another embodiment, the composition can comprise at least 8 distinct metabolites, including at least 4 distinct metabolites for individually modulating each one of white blood cells and neutrophils in a companion animal. In yet another embodiment, the composition can comprise at least 10 distinct metabolites, including at least 5 distinct metabolites for individually modulating each one of white blood cells and neutrophils in a companion animal. As such, in one aspect, the composition can comprise at least four distinct metabolites that modulate at least one of white blood cells or neutrophils. Further, in another aspect, the composition can comprise at least five distinct metabolites that modulate at least one of white blood cells or neutrophils. As previously noted, the metabolite configurations can be used for both method and composition embodiments.

In some embodiments, the metabolite negatively modulates the specific health parameter (i.e. white blood cells and neutrophils), and the changing of the amount of the metabolite comprises decreasing the amount of the metabolite. In other embodiments, the metabolite negatively modulates the specific health parameter, and the changing of the amount of the metabolite comprises increasing the amount of the metabolite. In some embodiments, the metabolite positively modulates the specific health parameter, and the changing of the amount of the metabolite comprises increasing the amount of the metabolite. In other embodiments, the metabolite positively modulates the specific health parameter, and the changing of the amount of the metabolite comprises decreasing the amount of the metabolite. These are not mutually exclusive embodiments; a particular embodiment can comprise decreasing the amount of a metabolite that negatively modulates a first specific health parameter and increasing the amount of a metabolite that positively modulates a second specific health parameter, and the first and second specific health parameter can be the same or different specific health parameter (e.g., one or more of white blood cells or neutrophils).

Decreasing the amount of the metabolite can comprise decreasing the amount of the metabolite directly and/or decreasing the amount of an ingredient which comprises the metabolite. In some embodiments, decreasing the amount of the metabolite can comprise decreasing the amount of a precursor of the metabolite directly and/or decreasing the amount of an ingredient which comprises a precursor of the metabolite. For example, the second formulation can contain, relative to the first formulation, less of an ingredient having a high amount of the metabolite or precursor thereof (e.g., an ingredient having an amount of the metabolite or precursor thereof that is higher than in one or more of the other ingredients).

Increasing the amount of the metabolite can comprise increasing the amount of the metabolite directly and/or increasing the amount of an ingredient which comprises the metabolite. In some embodiments, increasing the amount of the metabolite can comprise increasing the amount of a precursor of the metabolite directly and/or increasing the amount of an ingredient which comprises a precursor of the metabolite. For example, the second formulation can contain, relative to the first formulation, more of an ingredient having a high amount of the metabolite or precursor thereof (e.g., an ingredient having an amount of the metabolite or precursor thereof that is higher than in one or more of the other ingredients).

Generally, the methods and compositions described herein can provide an increase or a decrease in at least one of white blood cells or neutrophils in the companion animal. In some embodiment, the increase or decrease can be at least 5%, 10%, 15%, 20%, 25%, 30%, 35%, 40%, 45%, or even 50%. In one aspect, the compositions and methods can provide an increase. In another aspect, the compositions and methods can provide a decrease. In one embodiment, the increase or decrease can be for both white blood cells and neutrophils. As such, the present modulation, and resulting increase or decrease, can provide one of the following health benefits: increased immune health; increased immune response; improved immune response against bacteria, viruses and fungi; improved allergic response; improved immune response against cancer; increased immune response due to treatments including chemotherapy; decrease in stress; decrease in inflammation; decreased infection; improvement in skin health; improvement in autoimmune diseases including Crohn's or Grave's disease; improvement in stress recovery including exercise; improved response to trauma; and improved wound repair.

The cost of the pet food can be minimized and/or the nutritional benefit of the pet food can be enhanced by utilizing ingredients which are appropriately high in compounds which positively modulate the specific health parameter and/or appropriately low in compounds which negatively modulate the specific health parameter.

Ingredients comprising the metabolite (e.g., a precursor of the metabolite) and optionally amounts of the metabolite in the ingredient can be identified by analysis of the ingredient, for example using a separation technique, such as gas chromatography or liquid chromatography, and then mass spectrometry.

In each of these compositions and methods, the pet food composition can be a wet food, a semi-moist food or a dry food. In an embodiment, the pet food composition is one or more components of a blended composition. In some embodiments, the pet food composition is a kibble, and in some embodiments, the pet food composition is a meat analog. Additionally, in another embodiment, the present composition for modulating a specific health parameter can be a dietary supplement comprising the metabolites described herein. Further, a method of modulating a specific health parameter can include administering to the companion animal the dietary supplement.

Such pet food compositions can be administered to the companion animal in amounts ranging from about 3 g of pet food per 1 lb body weight to about 16 g of pet food per 1 lb body weight of the companion animal. Additionally, the metabolites can be present in amounts from about 0.01 weight % to about 10 weight % of the food composition. In one aspect, the metabolites can be present in concentrations of about 0.01 to about 1,000 mg/kg of food. In another aspect, the metabolites can be present in concentrations from about 1 IU to about 500,000 IU per kilogram of food. In one embodiment, the pet food composition can be administered to the companion animal in amounts sufficient to maintain the health and/or body weight of the animal. In one aspect, the administration can be regular administration.

As noted above and detailed later in this application, the present inventors identified metabolite compounds which correlate to white blood cells or neutrophils. Thus, the metabolite in the pet food composition can be one of these compounds. Nevertheless, the metabolite can be any metabolite for modulating at least one of white blood cells or neutrophils in a companion animal, even if the metabolite is not explicitly disclosed herein. For example, the metabolite can be a compound identified using the methods disclosed herein but not itself explicitly disclosed herein. Furthermore, the metabolite can be a compound identified using a method not disclosed herein if the compound is reliably correlated to at least one of white blood cells or neutrophils.

As a non-limiting example, the metabolite can modulate white blood cells and can be selected from the group consisting of X—12104, C-glycosyltryptophan, 3-ureidopropionate, erythronate, X—11945, isobutyrylcarnitine, X—11561, 2-hydroxyglutarate, arginine, 2-hydroxystearate, homocitrulline, pseudouridine, 1-linoleoylglycerophosphoinositol, cysteine, and mixtures thereof. In one embodiment, the metabolite can modulate white blood cells and can be selected from the group consisting of C-glycosyltryptophan, 3-ureidopropionate, erythronate, isobutyrylcarnitine, 2-hydroxyglutarate, arginine, 2-hydroxystearate, homocitrulline, pseudouridine, 1-linoleoylglycerophoinositol, and mixtures thereof.

As another non-limiting example, the metabolite can modulate neutrophils and can be selected from the group consisting of dimethylglycine, indoleacetate, 3-hydroxypropanoate, isobutyrylcarnitine, glycerate, phenyllactate (PLA), glycolate (hydroxyacetate), C-glycosyltryptophan, tryptophan, homocitrulline, and mixtures thereof. In one embodiment, the metabolite can modulate neutrophils and can be selected from the group consisting of dimethylglycine, indoleacetate, 3-hydroxypropanoate, isobutyrylcarnitine, glycerate, phenyllactate (PLA), and mixtures thereof.

In yet another aspect of the present disclosure, a method enhances nutritional benefit of a pet food having a first formulation designed for consumption by companion animals, and the method comprises administering the pet food having the first formulation to a first companion animal. The method further comprises measuring in a sample of body fluid from the companion animal (e.g., plasma) an amount of a surrogate marker comprising a metabolite that modulates at least one of white blood cells or neutrophils. The method further comprises adjusting the first formulation of the pet food to be a second formulation having a difference from the first formulation selected from the group consisting of (i) an ingredient is present in the second formulation and is absent in the first formulation, (ii) an ingredient is absent in the second formulation and is present in the first formulation, (iii) an ingredient is present in the first and second formulations but in a different amount, and (iv) combinations thereof. The adjusting is based at least partially on the amount of the surrogate marker measured in the previous step.

The adjusting can comprise directly decreasing the amount of a metabolite negatively modulating a specific health parameter (i.e. white blood cells or neutrophils) and/or decreasing the amount of an ingredient which comprises a metabolite negatively modulating a specific health parameter. In some embodiments, decreasing the amount of the metabolite can comprise decreasing the amount of a precursor of the metabolite directly and/or decreasing the amount of an ingredient which comprises a precursor of the metabolite. For example, the second formulation can contain, relative to the first formulation, less of an ingredient having a high amount of the metabolite or precursor thereof (e.g., an ingredient having an amount of the metabolite or precursor thereof that is higher than in one or more of the other ingredients).

The adjusting can comprise increasing the amount of the metabolite can comprise directly increasing the amount of a metabolite positively modulating a specific health parameter and/or increasing the amount of an ingredient which comprises a metabolite positively modulating a specific health parameter. In some embodiments, increasing the amount of the metabolite can comprise increasing the amount of a precursor of the metabolite directly and/or increasing the amount of an ingredient which comprises a precursor of the metabolite. For example, the second formulation can contain, relative to the first formulation, more of an ingredient having a high amount of the metabolite or precursor thereof (e.g., an ingredient having an amount of the metabolite or precursor thereof that is higher than in one or more of the other ingredients).

As noted above, ingredients comprising the metabolite (e.g., a precursor of the metabolite) and optionally amounts of the metabolite in the ingredient can be identified by analysis of the ingredient, for example using a separation technique, such as gas chromatography or liquid chromatography, and then mass spectrometry.

The method further comprises producing the pet food in the second formulation. In an embodiment, the method comprises administering the pet food having the second formulation to a second companion animal.

This method can be used to provide customized nutrition for a specific companion animal. For example, the first and second companion animal can be the same specific companion animal such that the animal who is administered the pet food having the first formulation has one or more of their specific health parameters of the first formulation assessed. Then this same animal is provided with the resultant second formulation which will increase at least one of white blood cells or neutrophils in the companion animal. Consequently, a pet owner can compensate for their pet's age-induced changes in one or more of white blood cells or neutrophils.

Alternatively or additionally, this method can be used to provide customized nutrition for companion animals who share one or more of a gender, an approximate age, an approximate size (e.g., body weight, height, and/or length) or a breed. For example, the second companion animal can be a different specific animal than the first companion animal but has a characteristic selected from the group consisting of (i) about the same age as the first companion animal, (ii) about the same size as the first companion animal, (iii) the same breed as the first companion animal, (iv) the same gender as the first companion animal, and (iv) combinations thereof. In one embodiment, the second companion animal can be one of a plurality of companion animals who each share the characteristic with the first companion animal. The method can comprise administering the pet food having the second formulation to the plurality of companion animals. In an embodiment, at least a portion of the plurality of companion animals is located remotely relative to the first companion animal.

The pet food compositions disclosed herein can be any food formulated for consumption by a pet such as a companion animal. In an embodiment, the pet food composition provides complete nutrition as defined by the Association of American Feed Control Officials (AAFCO) and which depends on the type of animal for which the composition is intended (e.g., dog or cat).

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

The pet food compositions disclosed herein can comprise vegetable oil, a flavorant, a colorant and water. Suitable vegetable oils include soybean oil, corn oil, cottonseed oil, sunflower oil, canola oil, peanut oil, safflower oil, and the like. Examples of suitable flavorants include yeast, tallow, rendered animal meals (e.g., poultry, beef, lamb, pork), flavor extracts or blends (e.g., grilled beef), animal digests, and the like. Suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as other grains and/or other starches additionally or alternatively to flour, amino acids, fibers, sugars, animal oils, aromas, other oils additionally or alternatively to vegetable oil, humectants, preservatives, polyols, salts, oral care ingredients, antioxidants, vitamins, minerals, probiotic microorganisms, bioactive molecules or combinations thereof.

Suitable starches include a grain such as corn, rice, wheat, barley, oats, soy and the like, and mixtures of these grains, and can be included at least partially in any flour. Suitable humectants include salt, sugars, propylene glycol and polyhydric glycols such as glycerin and sorbitol, and the like. Suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Examples of suitable antioxidants include butylated hydroxyanisole ("BHA") and butylated hydroxytoluene ("BHT"), vitamin E (tocopherols), and the like.

Non-limiting examples of vitamins that can be used include Vitamins A, B-complex (such as B-1, B-2, B-6 and B-12), C, D, E and K, niacin and acid vitamins such as pantothenic acid and folic acid and biotin. Non-limiting examples of suitable minerals include calcium, iron, zinc, magnesium, iodine, copper, phosphorus, manganese, potassium, chromium, molybdenum, selenium, nickel, tin, silicon, vanadium, boron and the like.

Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

For example, the amount of any of the above-noted ingredients can be decreased or increased based on the estimated effect on one or more of white blood cells or neutrophils (e.g., an effect identified by one of the methods disclosed herein). In an embodiment, the amount of one or more of the above-noted ingredients can be increased if such ingredients comprise a metabolite that positively modulates one or more of white blood cells or neutrophils. Additionally or alternatively, the amount of one or more of the above-noted ingredients can be decreased if such ingredients comprise a metabolite that negatively modulates one or more of white blood cells or neutrophils.

As noted above, ingredients comprising the metabolite (e.g., a precursor of the metabolite) and optionally amounts of the metabolite in the ingredient can be identified by analysis of the ingredient, for example using a separation technique, such as gas chromatography or liquid chromatography, and then mass spectrometry.

EXAMPLES

The following non-limiting examples are illustrative of embodiments of the present disclosure.

Methods

Each of the examples was derived from the following study.

83 Canines were all fed Diet A for 5 weeks, followed by a 1 week transition period and then 15 were fed Diet B for 5 weeks as shown in the Table 1 below. Plasma and whole blood samples were taken after overnight fasting using EDTA vacutainer tubes during the fifth week of feeding of each diet. After centrifugation, metabolomics plasma samples were aliquoted into cryovials and frozen at −80° C. White blood cells and neutrophil counts were determined using standard clinical blood count and differential blood count protocols.

TABLE 1

| Moisture Basis | Moisture % | DM % | Protein % | Fat % | Ash % | Fiber % | CHO % | GE kcal/g |
|---|---|---|---|---|---|---|---|---|
| Diet A | | | | | | | | |
| As-Is | 8.1 | 91.9 | 22.7 | 13.3 | 6.1 | 2.0 | 47.9 | 4.5 |
| Dry matter | 0 | 100 | 24.7 | 14.5 | 6.6 | 2.1 | 52.1 | 4.9 |
| Diet B | | | | | | | | |
| As-Is | 76 | 24 | 9.1 | 10.5 | 1.8 | 0 | 2.6 | 1.7 |
| Dry Matter | 0 | 100 | 38 | 43.7 | 7.5 | 0 | 10.8 | 6.9 |

Metabolomic analysis was carried out using the following methods by Metabolon Inc. Samples were extracted and split into equal parts for analysis on GC/MS and LC/MS/MS platforms. Proprietary software was used to match ions to an in-house library of standards for metabolite identification and for metabolite quantitation by peak area integration by Metabolon Inc. Mass and retention index are provided in the following tables such that each metabolite can be uniquely identified and individually distinguished.

At the time of analysis, samples were thawed and extracts prepared to remove protein, dislodge small molecules bound to protein or physically trapped in the precipitated protein matrix, and recover a wide range of chemically diverse metabolites. A separate aliquot of each experimental plasma sample was taken then pooled for the creation of "Client Matrix" (CMTRX) samples. These CMTRX samples were injected throughout the platform run and served as technical replicates, allowing variability in the quantitation of all consistently detected biochemicals to be determined and overall process variability and platform performance to be monitored. Extracts of all experimental and CMTRX samples were split for analysis on the GC/MS and LC/MS/MS platforms.

The CMTRX technical replicate samples were treated independently throughout the process as if they were client study samples. All process samples (CMTRX and Grob test mixtures of organic components used to assess GC column performance, process blanks, etc.) were spaced evenly among the injections for each day and all client samples were randomly distributed throughout each day's run. Data were collected over multiple platform run days and thus 'block normalized' by calculating the median values for each run-day block for each individual compound. This normalization minimizes any inter-day instrument gain or drift, but does not interfere with intra-day sample variability. Missing values (if any) were assumed to be below the level of detection for that biochemical with the instrumentation used and were imputed with the observed minimum for that particular biochemical.

A number of internal standards were added to each experimental and process standard sample just prior to injection into the mass spectrometers. A measure of the platform variability (7%) was determined by calculating the median relative standard deviation (RSD) for these internal standards. Because these standards are added to the samples immediately prior to injection into the instrument, this value reflects instrument variation. In addition, the median relative standard deviation (RSD) for the biochemicals that were consistently measured in the CMTRX represents the total variability within the process for the actual experimental samples and the variability in quantitation of the endogenous metabolites within these samples (12%). Results for the CMTRX and internal standards indicated that the platform produced data that met process specifications.

589 total metabolites were detected in plasma. This total corresponds to many biochemicals (401) that matched a named structure in the reference library (named compounds). The remaining biochemicals (188) represent distinct chemical entities (that is, they represent a single molecule of discrete molecular formula and structure), but they do not currently match a named biochemical in the reference library (unnamed/unknown compounds).

Example 1 (White Blood Cells)

Metabolite correlations with white blood cells were determined based on plasma metabolomics (Table 2). This provided a predictive model of compounds which can influence white blood cells either positively or negatively. Feeding different levels of these compounds (diet B vs diet A; Table 3), and noting changes in white blood cells (Table 4), served as a validation model. The metabolite compositions of the two different diets were determined to identify relative levels of specific compounds. Those validated by the model are shown in Table 5.

TABLE 2

Metabolite correlations with white blood cells. Correlations with a P value <0.01 are reported.

| ID | Correlation | Correlation P-Value | Retention Index | Mass |
|---|---|---|---|---|
| X-12104 | 0.5093 | 7.52E-07 | 1755 | 271.1 |
| C-glycosyltryptophan | 0.4819 | 3.46E-06 | 1912 | 367.1 |
| kynurenate | 0.4701 | 6.43E-06 | 2243 | 188.1 |
| cis-aconitate | 0.4679 | 7.18E-06 | 1461 | 192 |
| 3-ureidopropionate | 0.4599 | 1.08E-05 | 1062 | 133.1 |
| threitol | 0.4591 | 1.12E-05 | 1513 | 217.1 |
| erythronate | 0.4406 | 2.74E-05 | 1546.9 | 292.1 |
| N-acetylthreonine | 0.4334 | 3.81E-05 | 846 | 160.1 |
| X-11945 | 0.4229 | 6.14E-05 | 1896 | 283.1 |
| arabitol | 0.4133 | 9.34E-05 | 1687.5 | 307.1 |
| citrate | 0.4078 | 0.0001 | 1763.4 | 273.1 |
| X-12822 | 0.3924 | 0.0002 | 2786 | 389.1 |
| arabonate | 0.3876 | 0.0003 | 1736 | 292.1 |
| N-acetylmethionine | 0.3829 | 0.0003 | 1805 | 190.1 |
| X-15546 | 0.387 | 0.0003 | 1861 | 271.1 |
| X-17624 | 0.3719 | 0.0005 | 2913.8 | 267.2 |
| X-12263 | 0.3667 | 0.0006 | 1369 | 275.1 |
| X-12668 | −0.3652 | 0.0006 | 2318 | 246.1 |
| 3-aminoisobutyrate | 0.3634 | 0.0007 | 1252.2 | 101.9 |
| X-13835 | 0.3607 | 0.0007 | 1014 | 169.1 |
| isobutyrylcarnitine | 0.3581 | 0.0008 | 1941 | 232.2 |
| X-11561 | 0.3553 | 0.0009 | 1252 | 267.1 |
| allantoin | 0.3532 | 0.001 | 1809.8 | 518.3 |
| erythritol | 0.3489 | 0.0011 | 1517.5 | 217 |
| cystine | 0.3506 | 0.0011 | 2015.3 | 145.9 |
| X-11441 | −0.3468 | 0.0012 | 3773 | 331.1 |
| X-18558 | 0.3463 | 0.0013 | 1676.8 | 380.1 |
| X-11442 | −0.3462 | 0.0013 | 3902 | 331.1 |
| X-18487 | 0.3445 | 0.0013 | 1269.6 | 273.1 |
| xylonate | 0.3409 | 0.0015 | 1722 | 292 |
| N-acetylalanine | 0.342 | 0.0015 | 882 | 130.1 |
| gamma-glutamyltyrosine | 0.331 | 0.0021 | 2073 | 311.2 |
| N-acetyltryptophan | 0.3306 | 0.0021 | 2650 | 245.2 |
| X-12602 | 0.329 | 0.0022 | 1456 | 204.2 |
| indoleacrylate | −0.3274 | 0.0024 | 2529 | 186.1 |
| X-12721 | 0.3263 | 0.0025 | 1865 | 261 |
| X-11987 | 0.3262 | 0.0025 | 1409 | 139.2 |
| X-13695 | 0.3166 | 0.0033 | 2511 | 245 |
| 2-hydroxyglutarate | 0.3158 | 0.0034 | 1576 | 247 |
| arginine | −0.313 | 0.0037 | 728 | 173.2 |
| 2-hydroxystearate | 0.3086 | 0.0043 | 5705 | 299.4 |
| homocitrulline | 0.3071 | 0.0045 | 832 | 190.1 |
| pseudouridine | 0.3058 | 0.0047 | 1104 | 243.1 |

TABLE 2-continued

Metabolite correlations with white blood cells. Correlations with a P value <0.01 are reported.

| ID | Correlation | Correlation P-Value | Retention Index | Mass |
|---|---|---|---|---|
| N-acetyltyrosine | 0.3052 | 0.0048 | 1677 | 222.2 |
| 1-linoleoylglycerophosphoinositol | 0.3037 | 0.005 | 5487 | 595.3 |
| pentadecanoate (15:0) | −0.3027 | 0.0051 | 1853.5 | 299.2 |
| X-12189 | 0.3024 | 0.0052 | 1249 | 273.1 |
| X-11852 | −0.3016 | 0.0053 | 3324 | 233.1 |
| X-16975 | 0.2996 | 0.0056 | 2291.8 | 255.1 |
| X-11914 | 0.2959 | 0.0063 | 5448 | 295.3 |
| cysteine | 0.2954 | 0.0064 | 1560.1 | 218 |
| benzoate | −0.2945 | 0.0065 | 1291.5 | 179 |
| X-15636 | −0.2915 | 0.0071 | 3814 | 243.1 |
| gamma-glutamylphenylalanine | 0.2851 | 0.0086 | 2846 | 295.1 |
| N-acetylaspartate (NAA) | 0.2822 | 0.0093 | 1648.5 | 274 |
| X-15609 | 0.2824 | 0.0093 | 3664 | 273.1 |
| pro-hydroxy-pro | 0.2811 | 0.0096 | 960 | 229.2 |

TABLE 3

Compound levels present in diets A and B. Values represent scaled imputed values (data are scaled such that the median value measured across all samples was set to 1.0 and missing values (if any) were imputed with the observed minimum for that particular compound).

| ID | A | B |
|---|---|---|
| X-12104 | 0.51 | 1.13 |
| C-glycosyltryptophan | 0.72 | 2.79 |
| kynurenate | 0.21 | 0.21 |
| cis-aconitate | 0.34 | 0.34 |
| 3-ureidopropionate | 0.53 | 0.54 |
| threitol | 0.86 | 0.33 |
| erythronate | 0.58 | 0.63 |
| N-acetylthreonine | 0.22 | 0.22 |
| X-11945 | 0.53 | 0.64 |
| arabitol | 9.47 | 0.61 |
| citrate | 0.72 | 0.11 |
| X-12822 | 0.2 | 0.2 |
| arabonate | 4.02 | 1.03 |
| N-acetylmethionine | 2.66 | 0.29 |
| X-15546 | 0.15 | 0.15 |
| X-17624 | 0.19 | 0.19 |
| X-12263 | 0.14 | 0.14 |
| X-12668 | 0.13 | 0.13 |
| 3-aminoisobutyrate | 9.14 | 1.37 |
| X-13835 | 0.4 | 0.4 |
| isobutyrylcarnitine | 0.31 | 0.82 |
| X-11561 | 1.11 | 1.96 |
| allantoin | 0.28 | 0.05 |
| erythritol | 3.45 | 0.32 |
| cystine | 0.37 | 0.37 |
| X-11441 | 0.36 | 0.36 |
| X-18558 | 0.55 | 0.47 |
| X-11442 | 0.28 | 0.28 |
| X-18487 | 0.26 | 0.26 |
| xylonate | 8.82 | 8.21 |
| N-acetylalanine | 0.71 | 0.67 |
| gamma-glutamyltyrosine | 16.98 | 2.04 |
| N-acetyltryptophan | 1 | 0.24 |
| X-12602 | 0.23 | 0.23 |
| indoleacrylate | 0.06 | 0.06 |
| X-12721 | 0.29 | 0.29 |
| X-11987 | 0.14 | 0.14 |
| X-13695 | 0.11 | 0.11 |
| 2-hydroxyglutarate | 2.26 | 3.52 |
| arginine | 1 | 0.63 |
| 2-hydroxystearate | 0.76 | 0.79 |
| homocitrulline | 0.4 | 0.69 |
| pseudouridine | 0.07 | 0.1 |
| N-acetyltyrosine | 0.82 | 0.32 |
| 1-linoleoylglycerophosphoinositol | 2.57 | 2.64 |
| pentadecanoate (15:0) | 0.34 | 0.7 |

TABLE 3-continued

Compound levels present in diets A and B. Values represent scaled imputed values (data are scaled such that the median value measured across all samples was set to 1.0 and missing values (if any) were imputed with the observed minimum for that particular compound).

| ID | A | B |
| --- | --- | --- |
| X-12189 | 0.23 | 0.23 |
| X-11852 | 0.1 | 0.1 |
| X-16975 | 1.02 | 0.44 |
| X-11914 | 1.01 | 0.78 |
| cysteine | 0.21 | 0.24 |
| benzoate | 0.03 | 0.03 |
| X-15636 | 0.2 | 0.2 |
| gamma-glutamylphenylalanine | 14.27 | 1.36 |
| N-acetylaspartate (NAA) | 1.76 | 0.46 |
| X-15609 | 0.37 | 0.37 |
| pro-hydroxy-pro | 1.19 | 0.53 |

TABLE 4

White blood cells in response to diet A and Diet B.

| | Diet A | | Diet B | | Difference | | |
| --- | --- | --- | --- | --- | --- | --- | --- |
| Parameter | Mean | StdDev | Mean | StdDev | Mean | StdErr | p-value |
| White Blood Cells | 5.5 | 1.0 | 6.5 | 1.2 | −1.0 | 0.2 | 0 |

TABLE 5

Compounds validated by dietary change.

| ID | Retention Index | Mass |
| --- | --- | --- |
| X-12104 | 1755 | 271.1 |
| C-glycosyltryptophan | 1912 | 367.1 |
| 3-ureidopropionate | 1062 | 133.1 |
| erythronate | 1546.9 | 292.1 |
| X-11945 | 1896 | 283.1 |
| isobutyrylcarnitine | 1941 | 232.2 |
| X-11561 | 1252 | 267.1 |
| 2-hydroxyglutarate | 1576 | 247 |
| arginine | 728 | 173.2 |
| 2-hydroxystearate | 5705 | 299.4 |
| homocitrulline | 832 | 190.1 |
| pseudouridine | 1104 | 243.1 |
| 1-linoleoylglycerophosphoinositol | 5487 | 595.3 |
| cysteine | 1560.1 | 218 |

Example 2 (Neutrophils)

Metabolite correlations with neutrophils were determined based on plasma metabolomics (Table 6). This provided a predictive model of compounds which can influence neutrophils either positively or negatively. Feeding different levels of these compounds (diet B vs diet A; Table 7), and noting changes in neutrophils (Table 8), served as a validation model. The metabolite compositions of the two different diets were determined to identify relative levels of specific compounds. Those compounds validated by the model are shown in Table 9).

TABLE 6

Metabolite correlations with neutrophils. Correlations with a P value <0.01 are reported.

| ID | Correlation | Correlation P-Value | Retention Index | Mass |
| --- | --- | --- | --- | --- |
| 4-vinylphenol sulfate | −0.4171 | 2.14E−05 | 3323 | 199.1 |
| phenylalanyltryptophan | −0.3995 | 5.05E−05 | 3349 | 352.2 |
| 4-ethylphenylsulfate | −0.3681 | 0.0002 | 3570 | 201.1 |
| X-14352 | 0.3697 | 0.0002 | 2635 | 247.2 |
| dimethylglycine | 0.3571 | 0.0003 | 1030 | 57.9 |
| indoleacetate | −0.349 | 0.0005 | 3760 | 176.1 |
| X-13866 | −0.3445 | 0.0005 | 2406 | 253.1 |
| X-18570 | −0.3477 | 0.0005 | 3243.1 | 207 |
| X-11442 | −0.3424 | 0.0006 | 3902 | 331.1 |
| N-acetylmethionine | 0.338 | 0.0007 | 1805 | 190.1 |
| 3-methylhistidine | 0.34 | 0.0007 | 911 | 168.1 |
| 3-hydroxypropanoate | 0.3334 | 0.0008 | 1187.1 | 177.1 |
| X-11441 | −0.3342 | 0.0008 | 3773 | 331.1 |
| catechol sulfate | −0.3284 | 0.001 | 1928 | 188.9 |
| X-11437 | −0.3271 | 0.0011 | 2888 | 231 |
| threonate | 0.3205 | 0.0014 | 1560.7 | 292.1 |
| bilirubin (E,E) | −0.32 | 0.0014 | 4625 | 585.2 |
| N-acetyltyrosine | 0.314 | 0.0017 | 1677 | 222.2 |
| thromboxane B2 | −0.3111 | 0.0019 | 4520 | 369.3 |
| isobutyrylcarnitine | 0.3011 | 0.0027 | 1941 | 232.2 |
| histidine | −0.3 | 0.0028 | 757 | 154.1 |
| pro-hydroxy-pro | 0.2919 | 0.0037 | 960 | 229.2 |
| glycerate | 0.2917 | 0.0037 | 1360.7 | 189 |
| phenyllactate (PLA) | −0.2909 | 0.0038 | 2237 | 165.1 |
| glutamine | −0.2882 | 0.0042 | 684 | 147.2 |
| xylonate | 0.2856 | 0.0046 | 1722 | 292 |
| glycolate (hydroxyacetate) | 0.2852 | 0.0046 | 1119 | 177 |
| X-11530 | −0.2822 | 0.0051 | 4866 | 313.2 |
| C-glycosyltryptophan | 0.2778 | 0.0059 | 1912 | 367.1 |
| X-18218 | 0.2747 | 0.0065 | 2540.9 | 218 |
| 2-hydroxyisobutyrate | 0.2714 | 0.0072 | 1107.5 | 130.9 |
| 4-acetylphenol sulfate | −0.2704 | 0.0074 | 2399 | 215 |
| X-12339 | 0.2701 | 0.0074 | 1055 | 174.1 |
| tryptophan | −0.2698 | 0.0075 | 2445 | 205.1 |
| homocitrulline | 0.2687 | 0.0078 | 832 | 190.1 |
| equol sulfate | −0.2618 | 0.0096 | 3625 | 321.2 |
| X-16015 | −0.2616 | 0.0096 | 3788 | 268.1 |

TABLE 7

Compound levels present in diets A and B. Values represent scaled imputed values (data are scaled such that the median value measured across all samples was set to 1.0 and missing values (if any) were imputed with the observed minimum for that particular compound).

| ID | A | B |
| --- | --- | --- |
| 4-vinylphenol sulfate | 0.02 | 0.02 |
| phenylalanyltryptophan | 0.29 | 0.29 |
| 4-ethylphenylsulfate | 0.22 | 0.22 |
| X-14352 | 0.69 | 0.46 |
| dimethylglycine | 0.39 | 1.1 |
| indoleacetate | 1.78 | 0.46 |
| X-13866 | 0.26 | 0.26 |
| X-18570 | 0.08 | 0.08 |
| X-11442 | 0.28 | 0.28 |
| N-acetylmethionine | 2.66 | 0.29 |
| 3-methylhistidine | 0.26 | 0.76 |
| 3-hydroxypropanoate | 3.01 | 4.28 |
| X-11441 | 0.36 | 0.36 |
| catechol sulfate | 0.02 | 0.02 |
| X-11437 | 0.05 | 0.05 |
| threonate | 0.61 | 0.22 |
| bilirubin (E,E) | 0.32 | 0.32 |
| N-acetyltyrosine | 0.82 | 0.32 |
| thromboxane B2 | 0.24 | 0.24 |
| isobutyrylcarnitine | 0.31 | 0.82 |
| histidine | 0.31 | 0.45 |
| pro-hydroxy-pro | 1.19 | 0.53 |
| glycerate | 3.38 | 9.94 |
| phenyllactate (PLA) | 4.9 | 0.4 |

TABLE 7-continued

Compound levels present in diets A and B. Values represent scaled imputed values (data are scaled such that the median value measured across all samples was set to 1.0 and missing values (if any) were imputed with the observed minimum for that particular compound).

| ID | A | B |
|---|---|---|
| glutamine | 0.18 | 0.18 |
| xylonate | 8.82 | 8.21 |
| glycolate (hydroxyacetate) | 0.89 | 0.94 |
| X-11530 | 0.21 | 0.21 |
| C-glycosyltryptophan | 0.72 | 2.79 |
| X-18218 | 0.6 | 0.6 |
| 2-hydroxyisobutyrate | 0.51 | 0.51 |
| 4-acetylphenol sulfate | 0.4 | 0.56 |
| X-12339 | 0.96 | 0.5 |
| tryptophan | 0.29 | 0.18 |
| homocitrulline | 0.4 | 0.69 |
| equol sulfate | 0.08 | 0.08 |
| X-16015 | 0.02 | 0.02 |

TABLE 8

Neutrophils in response to diet A and Diet B.

| Parameter | Diet A | | Diet B | | Difference | | |
|---|---|---|---|---|---|---|---|
| | Mean | StdDev | Mean | StdDev | Mean | StdErr | p-value |
| Neutrophils % | 60.1 | 8.4 | 69.1 | 4.6 | −9 | 1.8 | 0 |

TABLE 9

Compounds validated by dietary change.

| ID | Retention Index | Mass |
|---|---|---|
| dimethylglycine | 1030 | 57.9 |
| indoleacetate | 3760 | 176.1 |
| 3-hydroxypropanoate | 1187.1 | 177.1 |
| isobutyrylcarnitine | 1941 | 232.2 |
| glycerate | 1360.7 | 189 |
| phenyllactate (PLA) | 2237 | 165.1 |
| glycolate (hydroxyacetate) | 1119 | 177 |
| C-glycosyltryptophan | 1912 | 367.1 |
| tryptophan | 2445 | 205.1 |
| homocitrulline | 832 | 190.1 |

It should be understood that various changes and modifications to the presently embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A pet food composition comprising:
protein, carbohydrates, fat, fiber, and at least 4 distinct metabolites including at least 2 distinct metabolites for modulating an amount of white blood cells in a companion animal and at least 2 distinct metabolites for modulating an amount of neutrophils in the companion animal;
wherein the at least 2 distinct metabolites for modulating the amount of white blood cells are selected from the group consisting of C-glycosyltryptophan, 3-ureidopropionate, erythronate, isobutyrylcarnitine, 2-hydroxyglutarate, arginine, 2-hydroxystearate, homocitrulline, pseudouridine, 1-linoleoylglycerophosphoinositol, cysteine, and mixtures thereof;
wherein the at least 2 distinct metabolites for modulating the amount of neutrophils are selected from the group consisting of dimethylglycine, indoleacetate, 3-hydroxypropanoate, isobutyrylcarnitine, glycerate, phenyllactate (PLA), glycolate (hydroxyacetate), C-glycosyltryptophan, tryptophan, homocitrulline, and mixtures thereof; and
wherein the at least 4 distinct metabolites are each present in amounts from about 0.01 weight % to about 10 weight % of the pet food composition.

2. The pet food composition of claim 1, wherein the at least 2 distinct metabolites for modulating the amount of white blood cells comprise at least 3 distinct metabolites for modulating the amount of white blood cells in the companion animal, and the at least 2 distinct metabolites for modulating the amount of neutrophils comprise at least 3 distinct metabolites for modulating the amount of neutrophils in the companion animal.

3. The pet food composition of claim 1, wherein the at least 2 distinct metabolites for modulating the amount of white blood cells comprise at least 4 distinct metabolites for modulating the amount of white blood cells in the companion animal, and the at least 2 distinct metabolites for modulating the amount of neutrophils comprise at least 4 distinct metabolites for modulating the amount of neutrophils in the companion animal.

4. The pet food composition of claim 1, wherein the at least 2 distinct metabolites for modulating the amount of white blood cells comprise at least 5 distinct metabolites for modulating the amount of white blood cells in the companion animal, and the at least 2 distinct metabolites for modulating the amount of neutrophils comprise at least 5 distinct metabolites for modulating the amount of neutrophils in the companion animal.

5. The pet food composition of claim 1, wherein the at least 2 distinct metabolites for modulating the amount of white blood cells are selected from the group consisting of C-glycosyltryptophan, 3-ureidopropionate, erythronate, isobutyrylcarnitine, 2-hydroxyglutarate, arginine, 2-hydroxystearate, homocitrulline, pseudouridine, 1-linoleoylglycerophosphoinositol, and mixtures thereof.

6. The pet food composition of claim 1, wherein the at least 2 distinct metabolites for modulating the amount of neutrophils are selected from the group consisting of dimethylglycine, indoleacetate, 3-hydroxypropanoate, isobutyrylcarnitine, glycerate, phenyllactate (PLA), and mixtures thereof.

7. A pet food composition comprising:
protein, carbohydrates, fat, fiber, and at least four metabolites, including C-glycosyltryptophan, 3-ureidopropionate, dimethylglycine and indoleacetate.

8. The pet food composition of claim 7, wherein at least one of the at least four metabolites is about 0.01 wt. % to about 10 wt. % of the pet food composition.

9. The pet food composition of claim 7, wherein at least two of the at least four metabolites are each about 0.01 wt. % to about 10 wt. % of the pet food composition.

10. The pet food composition of claim 7, wherein the at least four metabolites are each about 0.01 wt. % to about 10 wt. % of the pet food composition.

11. A pet food composition comprising:
protein, carbohydrates, fat, fiber, and at least 4 distinct metabolites including at least 2 distinct metabolites for modulating an amount of white blood cells in a companion animal and at least 2 distinct metabolites for modulating an amount of neutrophils in the companion animal;

wherein the at least 2 distinct metabolites for modulating the amount of white blood cells are selected from the group consisting of C-glycosyltryptophan, 3-ureidopropionate, erythronate, isobutyrylcarnitine, 2-hydroxyglutarate, arginine, 2-hydroxystearate, homocitrulline, pseudouridine, 1-linoleoylglycerophosphoinositol, cysteine, and mixtures thereof;

wherein the at least 2 distinct metabolites for modulating the amount of neutrophils are selected from the group consisting of dimethylglycine, indoleacetate, 3-hydroxypropanoate, isobutyrylcarnitine, glycerate, phenyllactate (PLA), glycolate (hydroxyacetate), C-glycosyltryptophan, tryptophan, homocitrulline, and mixtures thereof; and wherein the at least 4 distinct metabolites are present in amounts from about 0.01 mg/kg to about 1,000 mg/kg of the pet food composition.

* * * * *